United States Patent
Allen et al.

(10) Patent No.: US 9,558,448 B2
(45) Date of Patent: Jan. 31, 2017

(54) DYNAMIC INTERFACING IN A DEEP QUESTION ANSWERING SYSTEM

(71) Applicant: International Business Machines Corporation, Armonk, NY (US)

(72) Inventors: Corville O. Allen, Morrisville, NC (US); Adam T. Clark, Mantorville, MN (US); Jeffrey K. Huebert, Rochester, MN (US); Aspen L. Payton, Byron, MN (US); John E. Petri, St. Charles, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 183 days.

(21) Appl. No.: 14/185,432

(22) Filed: Feb. 20, 2014

(65) Prior Publication Data
US 2015/0235132 A1    Aug. 20, 2015

(51) Int. Cl.
| | |
|---|---|
| *G06N 3/08* | (2006.01) |
| *G06N 5/04* | (2006.01) |
| *G06F 17/30* | (2006.01) |
| *G06F 19/00* | (2011.01) |

(52) U.S. Cl.
CPC ......... *G06N 5/04* (2013.01); *G06F 17/30654* (2013.01); *G06F 17/30864* (2013.01); *G06F 19/363* (2013.01); *G06N 3/08* (2013.01)

(58) Field of Classification Search
None
See application file for complete search history.

(56) References Cited

U.S. PATENT DOCUMENTS

| | | |
|---|---|---|
| 2008/0282204 A1 | 11/2008 | Del Valle Lopez |
| 2013/0110847 A1 | 5/2013 | Sahuguet et al. |
| 2015/0234823 A1 | 8/2015 | Allen et al. |

OTHER PUBLICATIONS

Sheth, A Learning Approach to Personalized Information Filtering, Masters Thesis, Massachusetts Institute of Technology, 1994, pp. 1-76.*
Sheth, A Learning Approach to Personalized Information Filtering, Master of Science Thesis, Massachusetts Institute of Technology, 1994, pp. 1-76.*
Lison, Pierre; "Adaptive Dialogue Management for Human-Robot Interaction", Ph.D. thesis proposal, draft v0.1.

* cited by examiner

*Primary Examiner* — Wilbert L Starks
(74) *Attorney, Agent, or Firm* — Patterson+Sheridan, LLP

(57) ABSTRACT

System, method, and computer program product for performing an operation, the operation comprising analyzing a question submitted to a deep question answering system to determine a level of sophistication of the question, and modifying one or more subsequent communications issued by the deep question answering system based on the determined level of sophistication, wherein the modifying attempts to more closely match the determined level of sophistication of the question with a level of sophistication of the one or more subsequent communications.

11 Claims, 5 Drawing Sheets

101

```
User: I have a pain in my hand
Deep QA System: What area of your hand hurts?
User: My right hand
Deep QA System: Does your hand hurt when you make a fist?
User: No
Deep QA System: You may have a broken finger, please seek medical care
```

```
User: I have an acute pain in my metacarpus region
Deep QA System: Was a pressure test administered?
User: Yes
Deep QA System: Is there a rotational deformity?
User: No
Deep QA System: You may have a non-displaced fracture of a metacarpal,
please seek medical care
```

```
User: I have a pain in my metacarpus region
Deep QA System: Was a pressure test administered?
User: I'm not sure what that is
Deep QA System: You may have a broken hand, please seek medical care
```

FIG. 1C

DYNAMIC INTERFACING IN A DEEP QUESTION ANSWERING SYSTEM

BACKGROUND

Embodiments disclosed herein relate to the field of computer software. More specifically, embodiments disclosed herein relate to computer software that provides dynamic interfacing in deep question answering systems.

In deep question answering (deep QA) systems, a user interacts with the deep QA system by submitting a question and waiting for a response that includes one or more answers and supporting evidence. When the deep QA system detects that it cannot adequately complete a request, or that it can improve its answers with additional information, the deep QA system may ask the user to supply missing and/or clarifying information before fully processing the question. However, the current interface between the deep QA system and the user is static, and is not tailored to the user.

SUMMARY

Embodiments disclosed herein include at least a system, method, and computer program product for performing an operation, the operation comprising analyzing a question submitted to a deep question answering system to determine a level of sophistication of the question, and modifying one or more subsequent communications issued by the deep question answering system based on the determined level of sophistication, wherein the modifying attempts to more closely match the determined level of sophistication of the question with a level of sophistication of the one or more subsequent communications.

BRIEF DESCRIPTION OF THE SEVERAL VIEWS OF THE DRAWINGS

So that the manner in which the above recited aspects are attained and can be understood in detail, a more particular description of embodiments of the disclosure, briefly summarized above, may be had by reference to the appended drawings.

It is to be noted, however, that the appended drawings illustrate only typical embodiments of this disclosure and are therefore not to be considered limiting of its scope, for the disclosure may admit to other equally effective embodiments.

FIGS. 1A-1C illustrate techniques to implement dynamic interfacing in a deep question answering system, according to one embodiment.

DETAILED DESCRIPTION

Figure 2:
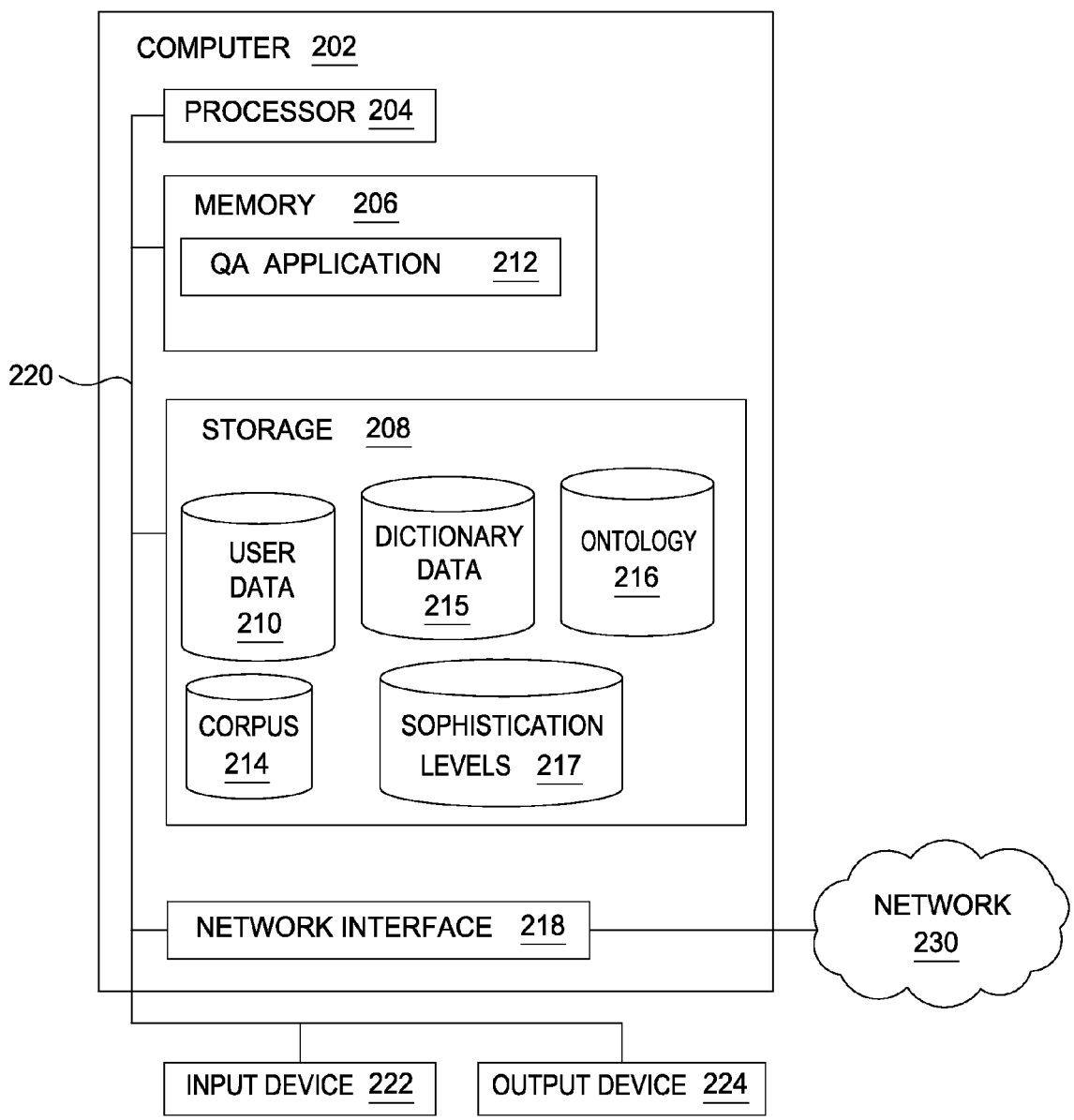
FIG. 2 is a block diagram illustrating a system implementing dynamic interfacing in a deep question answering system, according to one embodiment.

Embodiments disclosed herein dynamically change the interface between a deep question answering (deep QA) system and a user in response to ongoing dialogue with the user and/or recognizing the user's current environment. When the deep QA system receives a question from the user, the deep QA system may analyze the question in order to determine the level of sophistication of the question. For example, if the user's question reads "my tummy hurts," the deep QA system may determine that the question (and therefore the user) has a relatively low level of sophistication, while if the user says "I have an acute pain in my lower abdomen," the deep QA system may determine that the user has a high level of sophistication, relative to a baseline level of sophistication. In response, the deep QA system may dynamically modify subsequent communications it issues to the user. For example, and without limitation, the deep QA system may modify a number of questions presented to the user, modify a content of the questions presented to the user, or otherwise tailor the questions and responses to the questions based on the user's level of sophistication.

If the user has a high level of sophistication (as reflected by the input the user provides to the deep QA system), the deep QA system may skip certain questions targeted to users with of a lower level of sophistication. The deep QA system may also modify, based on the user's level of sophistication, the words in follow-up questions that are used to solicit additional information from the user, even though the deep QA system is seeking the same information from all levels of users. Additionally, the deep QA system may modify candidate answers returned to the user as responsive to the question based on the user's level of sophistication. For example, and without limitation, the deep QA system may return a diagnosis of "malignant melanoma" to a physician or other user with a high level of sophistication, while returning a diagnosis of "cancer" to users of lower levels of sophistication. Furthermore, any of the modifications described herein may be made based on an analysis of the user's current setting, or environment. For example, a user may call the deep QA system using a telephone while walking through a crowded area. The deep QA system may detect the background noise and determine that the user is in a rushed setting. In response, the deep QA system may reduce the number of follow-up questions presented the user in order to compact the duration of the user's session.

Generally, embodiments disclosed herein analyze user input to determine a level of sophistication of the input. The level of sophistication of the input may be imputed to the user. Therefore, the level of sophistication of the user and the input may be the same, and may be used interchangeably herein. As used herein, "sophistication" may be reflected by different attributes of the input, including, without limitation, vocabulary, grammar, and concepts in the input, as well as a level of skill, knowledge, or expertise of the user in a given subject as reflected by the input. As used herein, "communications" issued by a deep QA system refers to any output generated by the deep QA system and returned to a user. For example, the deep QA system may issue communications that include, without limitation, follow-up questions, clarifying questions, and responses to questions. As used herein, "dynamic interfacing" encompasses any type of modification to the communications, including, without limitation, questions asked by the deep QA system, a quantity of questions asked by the deep QA system, a content of the questions asked by the deep QA system, and a content of a response returned by the deep QA system. Generally, embodiments disclosed herein may modify any aspect of the interface between the user and the deep QA system in any way.

FIG. 1A illustrates techniques to implement dynamic interfacing in a deep question answering system, according to one embodiment. As shown, a dialogue box 101 reflects an example exchange between a user and a deep QA system. The user initially communicates to the deep QA system that "I have a pain in my hand." Upon receiving the question from the user, the deep QA system may analyze the question to determine the level of sophistication of the question (which may be imputed to the user). In at least some embodiments, the deep QA system assigns a default level of sophistication to the user. The default level of sophistication may be modified based on a domain/setting of the deep QA system. For example, if the deep QA system is targeted to medical workers (physicians, nurses, etc) in a hospital, the deep QA system may assume that the average user has a higher level of medical sophistication relative to the default levels of sophistication in medicine otherwise assigned to the general public.

In analyzing the user's question, the deep QA system may identify the word "hand" as being a term that is frequently used by lay people, and that the combination of words used indicates that the user does not have a medical background. In response, the deep QA system may ask clarifying questions that are tailored to the user. As shown, the deep QA system asks the user "what area of your hand hurts?" The deep QA system may have selected this question based on the user's level of sophistication in light the amount of information provided in the initial question, and may have modified the words (hand versus metacarpal, for example) to reflect the level of sophistication reflected in the user's question. The question itself may be tailored to a user with a low level of sophistication, as someone with a higher level of sophistication may have initially provided specific information (perhaps using medical terminology) that would have obviated the need to present such a follow-up question. When the user responds with "my right hand," the deep QA system may further refine the user's level of sophistication based on the sophistication of the user's response. For example, the deep QA system may detect that the user's response is not responsive to the question and includes terms used by lay people, and further lower the user's level of sophistication.

As shown, the deep QA system then asks the user "does your hand hurt when you make a fist?" The deep QA system may phrase and present this question based on the user's current level of sophistication. When the user responds with "no," the deep QA system has the requisite information needed to compute a response, and processes the user's case (also referred to as the question). After processing the case, the deep QA system may score multiple candidate answers, and return the highest scoring candidate answer as responsive to the question. In this example, the highest scoring candidate answer may indicate that the user has a "fractured phalange." However, the deep QA system may modify this response, which includes medical terminology, in order to match the user's level of sophistication. For example, as shown, the deep QA system may modify the candidate answer to indicate that "you may have a broken finger."

FIG. 1B illustrates techniques to implement dynamic interfacing in a deep question answering system, according to one embodiment. As shown, a dialogue interface 102 reflects an example exchange between a user and a deep QA system. The user initially communicates to the deep QA system that "I have an acute pain in my metacarpus region." Upon receiving the question from the user, the deep QA system may analyze the question to determine the user's level of sophistication. For example, the deep QA system may detect the presence "acute pain" and "metacarpus," and determine that these words indicate a high level of sophistication in the question. Furthermore, the deep QA system does not need to ask the user what part of the hand hurts, as the user specified "metacarpus." In response, the deep QA system may ask follow-up questions to the user reflecting the user's higher level of sophistication. As shown, the deep QA system asks whether a pressure test was administered and whether a rotational deformity exists before processing the question. After each response, the deep QA system may continue to update the user's level of sophistication based on the sophistication of each response. The deep QA system may then output a response in terms tailored to the user having the determined higher level of sophistication. As shown, the deep QA system indicates that the user "may have a non-displaced fracture of a metacarpal," which is targeted to the user having a higher level of sophistication.

FIG. 1C illustrates techniques to implement dynamic interfacing in a deep question answering system, according to one embodiment. As shown, a dialogue interface 103 reflects an example exchange between a user and a deep QA system. The user initially communicates to the deep QA system that "I have a pain in my metacarpus region." Upon receiving the question from the user, the deep QA system may analyze the question to determine the user's level of sophistication. The deep QA system, in analyzing this question, may determine that the user's use of the word "metacarpal" indicates a higher level of sophistication in the question, as this is the scientific word for the bone referred to by the user. As in FIG. 1B, the deep QA system asks a follow-up question tailored to a user with a higher level of sophistication, namely, whether a pressure test was administered. However, as shown, the user indicates that they are unaware of what a pressure test is. The deep QA system may reevaluate the user's level of sophistication, and determine that the user's response indicating a lack of knowledge as to a pressure test reflects a lower level of sophistication. As such, the deep QA system may reduce the user's level of sophistication, and proceed accordingly. Therefore, as shown, the user is not asked about a rotational deformity as in FIG. 1B. In addition, the deep QA system may modify the candidate answer returned as responsive by saying "you may have a broken hand," which uses the concepts of the returned response in FIG. 1B, however with language tailored to the user having a lower level of sophistication. Therefore, the response returned in FIG. 1C recites a "hand" versus the "metacarpal" of FIG. 1B. In addition, the response returned in FIG. 1C indicates that the hand may be "broken," rather than the "non-displaced fracture" of FIG. 1B.

In some embodiments, the user's level of sophistication may outweigh an incorrect or questionable response from the user. For example, the deep QA system may have been incorrect about the pressure test—perhaps there is no such thing as a pressure test, or the pressure test is traditionally administered to a different part of the body. If the user's response indicates, as in FIG. 1C, that they do not know what the pressure test is, instead of assuming that the user is unsophisticated for not knowing what a pressure test is, the deep QA system may override this assumption if the user's level of sophistication is relatively high. For example, if the deep QA system is only accessed by physicians in a hospital (and the user has not provided any evidence causing the deep QA system to otherwise reduce the user's level of sophistication), the deep QA system may not lower the user's level of sophistication, but instead correct itself, and use the exchange as training data. If the deep QA system sufficiently trusts the user's level of sophistication, and this response from the user is more of an anomaly, then the deep QA system may use the response as training data to correct itself for future cases. Continuing with this example, the deep QA system may train itself to not ask subsequent users whether a pressure test was administered in similar situations.

Furthermore, it should be noted that while the user's determined level of sophistication may change during a given session, the deep QA system may not automatically "shortcut" to a final answer. Instead, the deep QA system may reduce the complexity of follow-up questions in an attempt to acquire more detail on the user's case prior to presenting a final answer.

FIG. 2 is a block diagram illustrating a system 200 implementing dynamic interfacing in a deep question answering system, according to one embodiment. The networked system 200 includes a computer 202. The computer 202 may also be connected to other computers via a network 230. In general, the network 230 may be a telecommunications network and/or a wide area network (WAN). In a particular embodiment, the network 230 is the Internet.

The computer 202 generally includes a processor 204 connected via a bus 220 to a memory 206, a network interface device 218, a storage 208, an input device 222, and an output device 224. The computer 202 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 204 is included to be representative of a single CPU, multiple CPUs, a single CPU having multiple processing cores, and the like. Similarly, the memory 206 may be a random access memory. While the memory 206 is shown as a single identity, it should be understood that the memory 206 may comprise a plurality of modules, and that the memory 206 may exist at multiple levels, from high speed registers and caches to lower speed but larger DRAM chips. The network interface device 218 may be any type of network communications device allowing the computer 202 to communicate with other computers via the network 230.

The storage 208 may be a persistent storage device. Although the storage 208 is shown as a single unit, the storage 208 may be a combination of fixed and/or removable storage devices, such as fixed disc drives, solid state drives, floppy disc drives, tape drives, removable memory cards or optical storage. The memory 206 and the storage 208 may be part of one virtual address space spanning multiple primary and secondary storage devices.

The input device 222 may be any device for providing input to the computer 202. For example, a keyboard and/or a mouse may be used. The output device 224 may be any device for providing output to a user of the computer 202. For example, the output device 224 may be any conventional display screen or set of speakers. Although shown separately from the input device 222, the output device 224 and input device 222 may be combined. For example, a display screen with an integrated touch-screen may be used.

As shown, the memory 206 contains the QA application 212, which is an application generally configured to operate as a deep question answering (QA) system. One example of a deep question answering system is Watson, by the IBM Corporation of Armonk, N.Y. A user may submit a question (also referred to as a case) to the QA application 212, which will then provide an answer to the question based on an analysis of a corpus of information 214. The QA application 212 may analyze the question text to identify concepts (made up of one or more related words) in the question. Based on the analysis of the questions, the QA application 212 may identify a number of candidate answers. The QA application 212 may then find supporting evidence for the candidate answers. The QA application 212 may then score and rank the candidate answers, merge the results, and present the best answer as its response to the case.

Additionally, the QA application 212 may be configured to dynamically modify a dialogue interface based on a level of sophistication of the user, which may be reflected by the level of sophistication of the user's input to the QA application 212. Generally, the QA application 212 may analyze the level of sophistications of communications issued by a user in order to determine and refine the user's level of sophistication. The QA application 212 may store the computed sophistication levels for the user in the user data 210. In analyzing the user's communications, the QA application 212 may identify words and concepts used by the user in order to gain insights as to the user's level of sophistication. Generally, the QA application 212 may reference the corpus 214, one or more dictionaries 215, and one or more ontologies 216 in order to analyze the question. The terms in the user's questions and responses may be compared against terms in the dictionaries 215 and ontologies 216 to determine a level of sophistication associated with them. For example, "skin cancer" may be associated with a lower level of sophistication, while "malignant melanoma" is associated with a higher level of sophistication.

In addition, the QA application 212 may identify the sources of information in the corpus 214 that the terms, concepts, and phrases of the question appear. For example, the QA application 212 may compute inverse document frequency (IDF) scores indicating how frequently each term appears in different documents. For example, the QA application 212 may search the corpus 214, and determine that scholarly articles frequently reference "malignant melanoma," but that patient support forums have frequent references to "skin cancer." As such, the IDF score of "malignant melanoma" may be high in sources in the corpus 214 associated with a high level of sophistication (the scholarly articles), while being lower in sources associated with a lower level of sophistication (the support forums, for example). Likewise, the IDF score for "skin cancer" may be higher in sources in the corpus 214 associated with traditionally lower levels of sophistication (e.g., the user forums). In addition, the IDF score for "skin cancer" in the scholarly articles may be lower than the IDF score for "malignant melanoma." Therefore, the QA application 212 may determine that the user asking about "malignant melanoma" has a higher level of sophistication, while the user asking about "skin cancer" may have a lower level of sophistication.

Once the QA application 212 determines the user's level of sophistication, the QA application 212 may modify subsequent communications (the dialoguing interface) in order to match the user's level of sophistication. Generally, the QA application 212 may modify, without limitation, one or more of: the number of questions, the types of questions, the content of questions, the format of questions, and a format and/or a content of a response generated to the user's question. For example, if a user has a lower level of computer sophistication, the QA application 212 may ask whether their computer is plugged in. If the user has a higher level of computer sophistication, the QA application 212 may not ask the user whether their computer is plugged in, as the QA application 212 may presume that a computing expert would check to make sure that their computer is plugged in. In order to modify the content of follow-up questions and responses, the QA application 212 may reference the corpus 214, the dictionaries 215, and the ontologies 216 in order to find suitable replacements for the words and concepts the QA application 212 seeks to modify.

In addition, in some embodiments, the QA application 212 may modify the dialoguing interface based on the user's current environment. For example, the QA application 212 may detect that the user is calling from a quiet setting with no background noise, and conduct a regular dialoguing session. If, however, the QA application 212 detects loud noise in the background, the QA application 212 may skip some questions in order to keep the session brief. Generally, the QA application 212 may modify the dialoguing session based on the user's current environment, sophistication level, or both.

As shown, the storage 208 contains the user data 210, corpus 214, dictionaries 215, ontologies 216, and sophistication levels 217. The user data 210 is a data store that includes information related to a plurality of different users. The user data 210 may include user profiles that reflect the user's level of sophistication in any number of different areas, as computed by the QA application 212. For example, one user may be an expert in sociology, but a novice in computer networking. The corpus 214 is a body of information used by the QA application 212 to generate answers to cases. For example, the corpus 214 may contain scholarly articles, dictionary definitions, encyclopedia references, and the like. The dictionaries 215 may include one or more dictionaries that define different terms in one or more disciplines. The ontologies 216 include one or more ontologies providing a structural framework for organizing information. An ontology formally represents knowledge as a set of concepts within a domain, and the relationships between those concepts. The sophistication levels 217 may include one or more baseline levels of sophistication, as well as acceptable values for each area of sophistication. The areas of sophistication may correspond to ontology levels, such as a general medical ontology, or different sub-sections of the medical ontology, such as an oncologist or general practitioner sub-section of the ontology. Generally, the representation of the user's level of sophistication in the sophistication levels 217 (and the user data 210) may take any format suitable to represent one or more different levels of sophistication. Furthermore, the QA application 212 may implement any feasible algorithm in order to compute a value for the user's level of sophistication.

Figure 3:
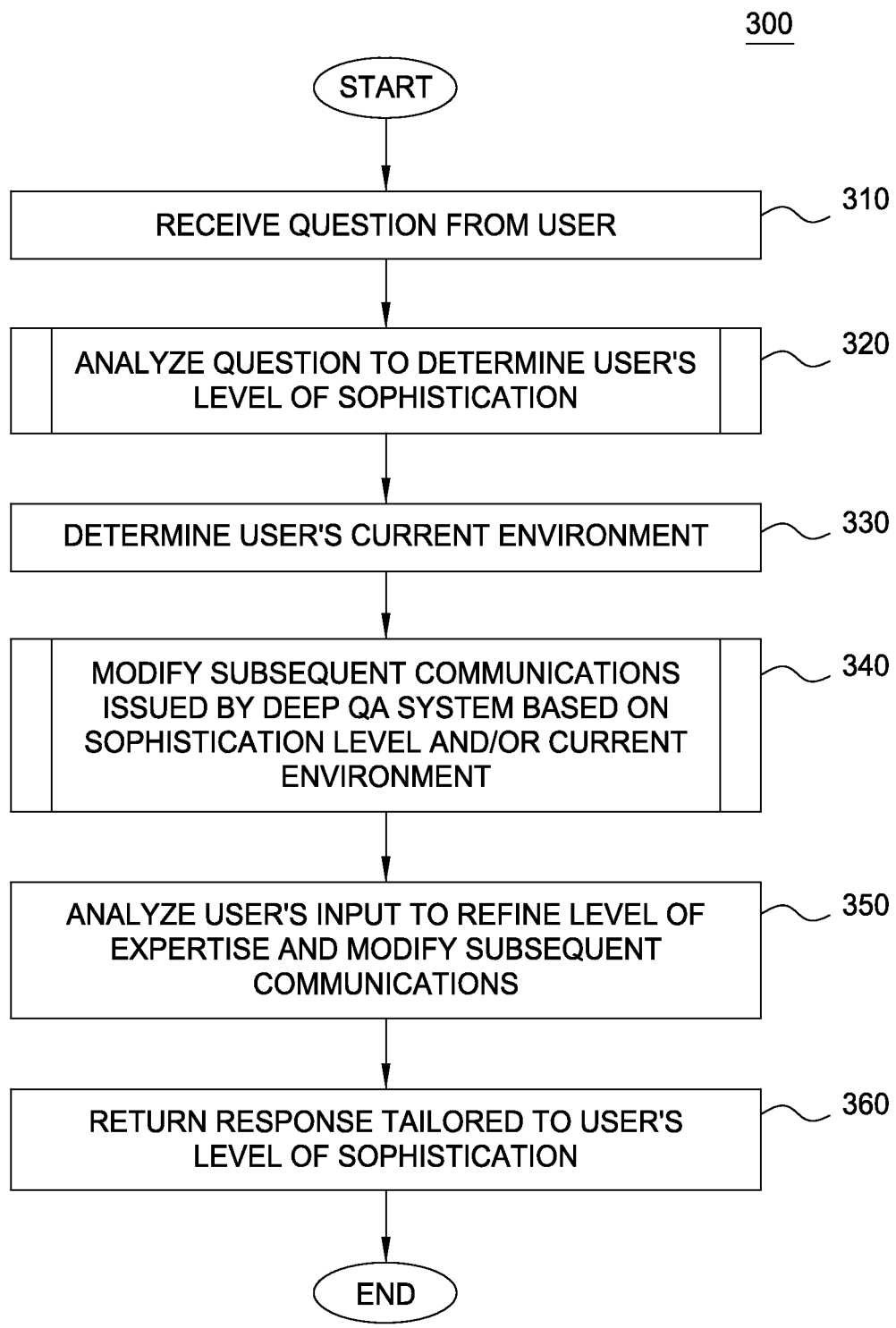
FIG. 3 is a flow chart illustrating a method for dynamic interfacing in a deep question answering system, according to one embodiment.

FIG. 3 is a flow chart illustrating a method 300 for dynamic interfacing in a deep question answering system, according to one embodiment. Generally, the QA application 212 may execute the steps of the method 300 in order to provide an enhanced experience that is tailored to users, their sophistication levels, and/or their current environment. At step 310, the QA application 212 may receive a question from a user. For example, the user may tell the QA application 212 that "my Internet is broken." At step 320, the QA application 212 analyzes the question to determine the user's level of sophistication. Generally, the QA application 212 may implement any number of techniques to determine the level of sophistication. For example, and without limitation, the QA application 212 may identify uncertainty and unfamiliarity on the part of the user if the user omitted relevant information from the question or included ambiguous information in the question. The user's question indicating that the "Internet is broken" omits information that could be relevant to solving the problem. Furthermore, the QA application 212 may analyze the words and concepts in the question in order to determine a corresponding level of sophistication associated with those words and concepts. Continuing with the Internet example, the term "broken" is not typically used by an expert in computing to address Internet connectivity issues, and indicates that the user is not very proficient in this field. At step 330, the QA application 212 may determine the user's current environment, as the QA application 212 may use the user's current environment in order to modify its dialoguing interface. For example, if the user types very tersely, the QA application 212 may determine that the user is in a hurry and that the QA application 212 should keep the duration of the session to a minimum by not asking too many questions of the user. Furthermore, if the QA application 212 is being used to answer questions received from medical professionals at a hospital, the QA application 212 may communicate with the medical professionals using a vernacular associated with the medical profession, while using layman terms to answer questions received from a publicly accessible website.

At step 340, described in greater detail with reference to FIG. 4, the QA application 212 modifies subsequent communications based on the computed sophistication level and/or current environment of the user. At step 350, the QA application 212 continues to analyze a level of sophistication of input provided by the user in order to continuously refine the user's level of sophistication and modify subsequent communications. Generally, the user's level of sophistication may be modified over time as the user provides additional insight as to their true level of sophistication. Therefore, the QA application 212 may continuously analyze the user's input in order to refine the user's level of sophistication. At step 360, the QA application 212 returns a response to the question tailored to the user's most recently computed level of sophistication. For example, the QA application 212 may modify "malignant melanoma" in a generated response to read "cancer" if the QA application 212 determines that the user is a lay person in the field of medicine.

Figure 4:
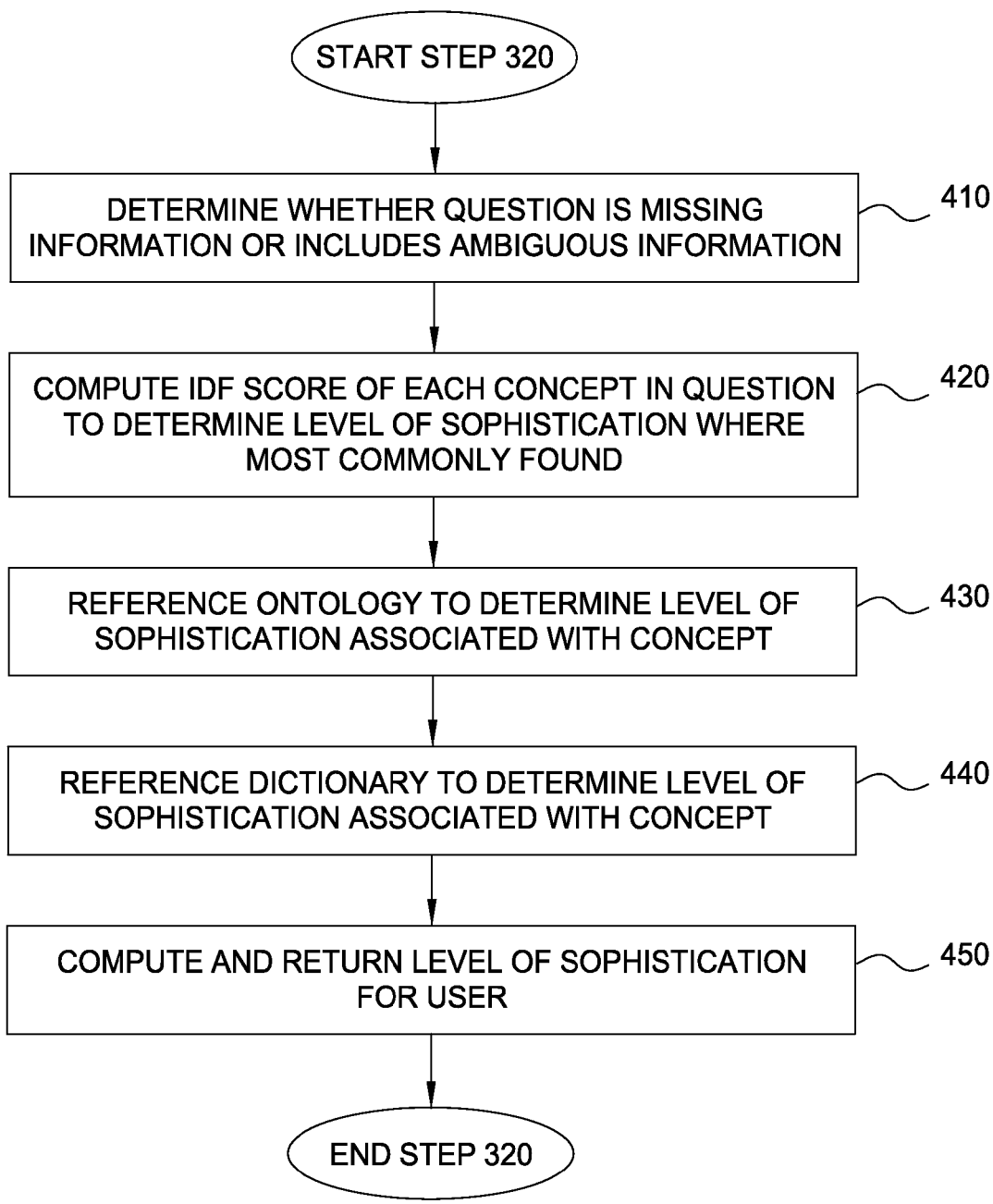
FIG. 4 is a flow chart illustrating a method to determine a user's level of sophistication, according to one embodiment.

FIG. 4 is a flow chart illustrating a method 400 corresponding to step 330 to determine a user's level of sophistication, according to one embodiment. Generally, the QA application 212 performs dialog analysis through the steps of the method 400 in order to identify the user's level of sophistication. Although depicted as a flow chart, the QA application 212 may not execute each step of the method 400 in each invocation of the method. Instead, the QA application 212 may execute one or more steps of the method 400 in order to determine the user's level of sophistication. In addition, the QA application 212 may invoke the method 400 multiple times during the same question/answering session with a user in order to refine the user's level of sophistication based on all input provided by the user, not just the initial question. At step 410, the QA application 212 determines whether the question is missing information, or includes ambiguous information, in order to identify uncertainty or unfamiliarity from the user. Generally, missing or ambiguous information may indicate an unsophisticated question, reflecting that the user is not an expert in the field. As such, the QA application 212 may not assign a high level of sophistication to a user who does not include relevant information or provides ambiguous information. Conversely, if the user provides detailed, relevant, and technical information, the QA application 212 may determine, based on the sophistication of the question, that the user is well versed in the field, and may have higher than normal sophistication.

At step 420, the QA application 212 may compute IDF scores of each concept in the question in order to determine where the concepts are most commonly used, and a level of sophistication associated with the sources of information using these concepts most frequently. For example, if the user's question asks when the next "vernal equinox" will occur, the QA application 212 may determine that "vernal equinox" occurs most frequently in scholarly articles related to astronomy, and that the user may have a higher level of sophistication in this field. However, if the user asks for when "daytime and nighttime are the same length," these quoted concepts may not appear frequently in scholarly articles, but instead more frequently in general knowledge bases that are not associated with sophistication in astronomy. Therefore, the QA application 212 may modify the user's level of sophistication accordingly.

At step 430, the QA application 212 may reference an ontology to determine a level of sophistication associated with each concept in the question. For example, a term such as "malignant melanoma" may be a specific node in a medical ontology, which may indicate that the term is associated with a higher level of sophistication. However, the term "skin cancer" may be a higher level concept in the ontology, which may reflect a lower level of sophistication. In some embodiments, the QA application 212 may attempt to indicate sophistication by exploring how many concepts in the ontology are related to the current concepts by being child-concepts of the current concepts. If an ontology has many concepts identified as more specific concepts of the current concept, then the QA application 212 may identify the current concept as vague (such as cancer), but if it has very few child-concepts, the QA application 212 may consider the current concept to be very specific (such as a malignant melanoma of the left ear lobe). At step 440, the QA application 212 may reference a dictionary in order to determine a level of sophistication associated with a word or concept presented by the user. For example, if a term is not referenced in a general purpose dictionary, but is instead found in a dictionary associated with a specific scientific discipline, the QA application 212 may determine that the fact that the user used the word indicates a higher level of sophistication in the scientific discipline. At step 450, the QA application 212 computes the level of sophistication for the user using the information obtained at steps 410-440. Generally, the QA application 212 may compute the score using any algorithm sufficient to produce one or more values that are within a range of acceptable values reflecting different levels of sophistication. For example, the QA application 212 may weigh the heuristics of steps 410-440 according to a predefined weighting scheme in order to compute a numeric score between 0-100 reflecting the user's sophistication.

Figure 5:
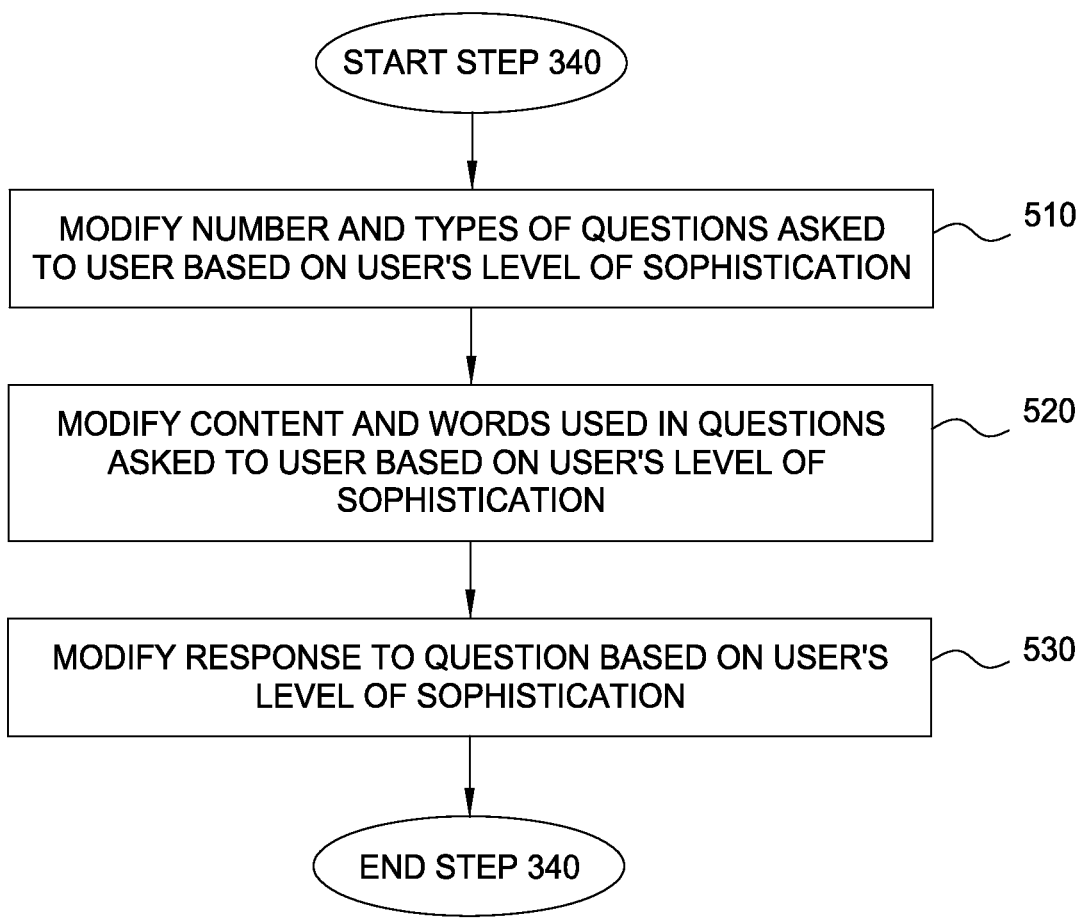
FIG. 5 is a flow chart illustrating a method to modify subsequent communications issued by a deep question answering system, according to one embodiment.

FIG. 5 is a flow chart illustrating a method 500 corresponding to step 340 to modify subsequent communications issued by a deep question answering system based on the user's level of sophistication and/or the user's current environment, according to one embodiment. Generally, the QA application 212 may execute the steps of the method 500 in order to modify any aspect of the user interface when the user asks a question of the QA application 212. At step 510, the QA application 212 may modify the number and/or the type of questions asked to the user based on the user's level of sophistication. For example, the QA application 212 may "skip ahead" when the user has a high level of sophistication. Stated differently, the QA application 212 may not ask basic questions the QA application 212 may normally ask to users not having a high level of sophistication. For example, the QA application 212 may be used to aid technical support for an Internet provider. If the QA application 212 determines that the user has a high level of sophistication based on their input to the system, the vocabulary they use, and the like, the QA application 212 may skip basic troubleshooting questions such as "are your cables are plugged in" and forego basic solutions such as "reset your modem," "reboot your PC," and the like. However, if the QA application 212 determines that the user has a low level of sophistication with computers, the QA application 212 may still ask these basic follow-up questions and/or present the basic solutions to the user having low sophistication. At step 520, the QA application 212 may modify the content and words of follow-up questions presented to the user based on the user's level of sophistication. For example, if the QA application 212 determines that it needs the user to provide additional clarifying information, it may modify the words it uses to ask for the additional information. Therefore, the QA application 212 may ask a computing novice "is your computer plugged in," while asking a computing expert "is the device powered on?" At step 530, the QA application 212 may modify the response it presents to the user based on the user's level of sophistication. For example, if the QA application 212 determines that the most likely reason the user cannot connect to the Internet because of a bad Ethernet cable, the QA application 212 may tell the computing novice to "replace the cable from your computer to the modem," while informing the expert "you need a new cat-6 Ethernet cable."

Advantageously, embodiments disclosed herein tailor communications between a deep question answering system and a user to match the user's computed level of sophistication. By determining a level of sophistication of the user's input, the deep QA system may determine the user's level of sophistication, and modify follow-up questions, responses, and any other communications based on the user's level of sophistication. The deep QA system may provide an enhanced user experience by not burdening users of higher levels of sophistication with questions aimed at users with lower levels of sophistication, while ensuring that users of lower levels of sophistication are not confused in obtaining a response to their question. Generally, the deep QA system may omit some questions, alter a content and type of the questions, and tailor the language of questions and the responses generated in order to match the user's level of sophistication. Further still, the deep QA system may consider the user's current environment in modifying the dialogue interface.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications or related data available in the cloud. For example, the QA application 212 could execute on a computing system in the cloud and process questions presented by users. In such a case, the QA application 212 could determine a user's level of sophistication, and store the determined level of sophistication at a storage location in the cloud. Doing so allows a user to access this information from any computing system attached to a network connected to the cloud (e.g., the Internet).

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A system, comprising:
   one or more computer processors; and
   a memory containing a program which when executed by the one or more computer processors, performs an operation comprising:
      assigning, by a question answering (QA) system, a first level of sophistication, of a plurality of levels of sophistication, to a question answering session, wherein each level of the plurality of levels of sophistication of the question answering session reflects a respective vocabulary in communications issued by the QA system;
      analyzing a question submitted to the QA system to determine a level of sophistication of the question, wherein the level of sophistication of the question reflects a vocabulary used in the question;
      assigning, by the QA system, a second level of sophistication, of the plurality of levels of sophistication, to the question answering session based on the determined level of sophistication of the question;
      determining a current environment of a user submitting the question;
      assigning a third level of sophistication, of the plurality of levels of sophistication, to the question answering session based on the current environment of the user; and
      modifying a communication issued by the QA system based on the third level of sophistication of the question answering session.

2. The system of claim 1, the operation further comprising:
   modifying, based on the second level of sophistication, a content of a question issued by the QA system responsive to receiving the question.

3. The system of claim 1, the operation further comprising:
   modifying, based on the second level of sophistication, a content of an answer generated by the QA system as being responsive to the question.

4. The system of claim 1, wherein analyzing the question comprises at evaluating a content of the question to identify a word indicating the level of sophistication of the question, wherein the content of the question is evaluated by: (i) computing an inverse document frequency (IDF) score of the word in one or more domains to identify a first domain in which the word is most commonly used, (ii) identifying the word in an ontology indicating a relationship between the word and one or more other concepts, (iii) referencing a dictionary to determine at least one of a field of use and a meaning of the word.

5. The system of claim 1, the operation further comprising:
   subsequent to receiving a response to a modified communication issued by the QA system:
      analyzing the response to determine a level of sophistication of the response;
      assigning a third level of sophistication, of the plurality of levels of sophistication, to the question answering session based on the level of sophistication of the response and the second level of sophistication for the question answering session; and
      modifying a subsequent communication issued by the QA system subsequent to the received response based on the third level of sophistication for the question answering session.

6. The system of claim 1, wherein modifying the communication comprises:
   modifying a number of questions issued by the question answering system responsive to the submitted question, wherein the question answering system does not issue a first question responsive to the submitted question upon determining that the third level of sophistication does not match a level of sophistication of the first question.

7. A computer program product, comprising:
   a computer-readable storage medium having computer-readable program code embodied therewith, the computer-readable program code executable by a processor to perform an operation comprising:
      assigning, by a question answering (QA) system, a first level of sophistication, of a plurality of levels of sophistication, to a question answering session, wherein each level of the plurality of levels of sophistication of the question answering session reflects a respective vocabulary in communications issued by the QA system, wherein the first level of sophistication is associated with: (i) a location where the QA system is deployed, and (ii) a set of users at the location;
      analyzing a question submitted to the QA system to determine a level of sophistication of the question, wherein the level of sophistication of the question reflects a vocabulary used in the question;
      assigning, by the QA system, a second level of sophistication, of the plurality of levels of sophistication, to the question answering session based on the determined level of sophistication of the question; and
      modifying, based on the second level of sophistication, a number of questions issued by the question answering system responsive to receiving the question, wherein the question answering system does not issue a first question responsive to receiving the question upon determining that the second level of sophistication does not match a level of sophistication of the first question.

8. The computer program product of claim 7, the operation further comprising:
   modifying, based on the second level of sophistication, a content of a question issued by the QA system responsive to receiving the question.

9. The computer program product of claim 7, the operation further comprising:

modifying, based on the second level of sophistication, a content of an answer generated by the QA system as being responsive to the question.

10. The computer program product of claim 7, wherein analyzing the question comprises at evaluating a content of the question to identify a word indicating the level of sophistication of the question, wherein the content of the question is evaluated by: (i) computing an inverse document frequency (IDF) score of the word in one or more domains to identify a first domain in which the word is most commonly used, (ii) identifying the word in an ontology indicating a relationship between the word and one or more other concepts, (iii) referencing a dictionary to determine at least one of a field of use and a meaning of the word.

11. The computer program product of claim 7, the operation further comprising:
- subsequent to receiving a response to a modified communication issued by the QA system:
  - analyzing the response to determine a level of sophistication of the response;
  - assigning a third level of sophistication, of the plurality of levels of sophistication, to the question answering session based on the level of sophistication of the response and the second level of sophistication for the question answering session; and
  - modifying a subsequent communication issued by the QA system subsequent to the received response based on the third level of sophistication for the question answering session.

* * * * *